(12) United States Patent
Zarkesh-Ha et al.

(10) Patent No.: US 11,008,611 B2
(45) Date of Patent: May 18, 2021

(54) DOUBLE GATE ION SENSITIVE FIELD EFFECT TRANSISTOR

(71) Applicant: UNM Rainforest Innovations, Albuquerque, NM (US)

(72) Inventors: Payman Zarkesh-Ha, Albuquerque, NM (US); Steven R. J. Brueck, Albuquerque, NM (US); Jeremy Edwards, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 929 days.

(21) Appl. No.: 14/347,713

(22) PCT Filed: Sep. 28, 2012

(86) PCT No.: PCT/US2012/057758
§ 371 (c)(1),
(2) Date: Mar. 27, 2014

(87) PCT Pub. No.: WO2013/049463
PCT Pub. Date: Apr. 4, 2013

(65) Prior Publication Data
US 2014/0234981 A1     Aug. 21, 2014

Related U.S. Application Data

(60) Provisional application No. 61/542,013, filed on Sep. 30, 2011, provisional application No. 61/550,166, filed on Oct. 21, 2011.

(51) Int. Cl.
*G01N 27/00* (2006.01)
*G01N 27/414* (2006.01)
(Continued)

(52) U.S. Cl.
CPC ......... *C12Q 1/6869* (2013.01); *C12Q 1/6806* (2013.01); *C12Q 1/6874* (2013.01);
(Continued)

(58) Field of Classification Search
CPC .. C12Q 1/6869; C12Q 1/6806; C12Q 1/6874; C12Q 2531/125; Y10T 436/143333; G01N 27/4145; G01N 27/414
(Continued)

(56) References Cited

U.S. PATENT DOCUMENTS 4,589,970 A * 5/1986 Ligtenberg ......... G01N 27/4141
204/406
7,462,512 B2    12/2008 Levon et al.
(Continued)

OTHER PUBLICATIONS

Written Opinion of the International Search Authority dated Mar. 11, 2013, for related application PCT/US2012/057758.
(Continued)

*Primary Examiner* — Rebecca M Fritchman
(74) *Attorney, Agent, or Firm* — Mueting Raasch Group (57) ABSTRACT

Devices that include a substrate; a source region and a drain region formed within the substrate and having a channel region provided therebetween; a first insulating layer formed over the channel region; a first floating gate formed over the first insulating layer, the first floating gate configured to respond to an analyte in a target material; and a second gate formed over the first floating gate, the second gate capacatively coupled but not electrically connected to the first floating gate.

7 Claims, 2 Drawing Sheets

(51) Int. Cl.
    *C12Q 1/6869* (2018.01)
    *C12Q 1/6806* (2018.01)
    *C12Q 1/6874* (2018.01)
(52) U.S. Cl.
    CPC ....... *G01N 27/414* (2013.01); *G01N 27/4145* (2013.01); *Y10T 436/143333* (2015.01)
(58) Field of Classification Search
    USPC .......................................................... 436/94
    See application file for complete search history.

(56) References Cited

U.S. PATENT DOCUMENTS

| | | |
|---|---|---|
| 2005/0230271 A1 | 10/2005 | Levon et al. |
| 2006/0016699 A1 | 1/2006 | Kamahori et al. |
| 2009/0017453 A1 | 1/2009 | Maples et al. |
| 2009/0108831 A1 | 4/2009 | Kalle et al. |
| 2009/0127589 A1 | 5/2009 | Rothberg et al. |
| 2010/0137143 A1 | 6/2010 | Rothberg et al. |
| 2010/0200781 A1* | 8/2010 | Khorasani ......... B01L 3/502715 250/576 |
| 2011/0299337 A1 | 12/2011 | Parris et al. |

OTHER PUBLICATIONS

International Preliminary Report on Patentability dated Apr. 1, 2014, for related application PCT/US2012/057758.
International Search Report dated Mar. 11, 2013 for related application PCT/US2012/057758.
Adey et al. "Rapid, low-input, low-bias construction of shotgun fragment libraries by high-density in vitro transposition". 2010. *Genome Biology.* 11:R119. (17 pages).
Akeson et al. "Microsecond time-scale discrimination among polycytidylic acid, polyadenylic acid, and polyuridylic acid as homopolymers or as segments within single RNA molecules". 1999. *Biophysical Journal.* 77:3227-3233.
Allen et al. "Robust testing of haplotype/disease association". 2005. *BMC Genet* 6:Suppl 1, S69. (5 pages).
Allen et al. "Single virus genomics: a new tool for virus discovery". 2011. *PLoS ONE* 6(3):e17722. (9 pages).
Alsmadi et al. "Haplotypes encompassing the KIAA0391 and PSMA6 gene cluster confer a genetic link for myocardial infarction and coronary artery disease". 2009. *Ann Hum Genet* 73:475-483.
Altshuler et al. "An SNP map of the human genome generated by reduced representation shotgun sequencing". 2000. *Nature.* 407:513-516.
Alsmadi et al. "Specific and complete human genome amplification with improved yield achieved by phi29 DNA polymerase and a novel prime at elevated temperature". 2009. *BMC Res Notes.* 2:48. (8 pages).
Anna et al. "Formation of dispersions using "flow focusing" in microchannels". 2003. *Applied Physics Letters.* 82(3):364-366.
Aviel-Ronen et al. "Large fragment Bst DNA polymerase for whole genome amplification of DNA from formalin-fixed paraffin-embedded tissues". 2006. *BMC genomics.* 7:312. (10 pages).
Arzumanyan et al. "Pathogenic mechanisms in HBV-and HCV-associated hepatocellular carcinoma". 2013. *Nature Reviews/Cancer.* 13:123-135.
Bentley et al. "Accurate whole human genome sequencing using reversible terminator chemistry". 2008. *Nature.* 456(7218):53-59.
Bergen et al. "Comparison of yield and genotyping performance of multiple displacement amplification and OmniPlex™ whole genome amplified DNA generated from multiple DNA sources". 2005. *Hum Mutat.* 26(3):262-270.
Bergen et al. "Effects of DNA mass on multiple displacement whole genome amplification and genotyping performance". 2005. *BMC Biotechnol.* 5:24. (11 pages).

Bergveld. "Thirty years of ISFETOLOGY: What happened in the past 30 years and what may happen in the next 30 years". 2003. *Sensors and Actuators B: Chemical.* 88:1-20.
Bi et al. "Design and synthesis of a chemically cleavable fluorescent nucleotide, 3'O-allyl-dGTP-allyl-bodipy-FL-510, as a reversible terminator for DNA sequencing by synthesis". 2006. *J Am Chem Soc* 128:2542-2543.
Bibette et al. "Stability criteria for emulsions". 1992. *Phys. Rev. Lett.* 69(16):2439-2442.
Botstein et al. "Discovering genotypes underlying human phenotypes: past successes for mendelian disease, future approaches for complex disease". 2003. *Nat. Genet.* 33:228-237.
Bouvard. "The Human Papillomavirus Type 16 E5 Gene Cooperates with the E7 Gene to Stimulate Proliferation of Primary Cells and Increases Viral Gene Expression". Virology. 1994. pp. 73-80.
Bowers et al. "Virtual terminator nucleotides for next-generation DNA sequencing". 2009. *Nature Methods.* 6(8):593-595.
Branton et al. "The potential and challenges of nanopore sequencing". 2008. *Nature Biotechnology.* 26(10):1146-1153.
Browning et al. "Haplotype phasing: existing methods and new developments". 2011. *Nat Rev Genet* 12(10):703-714.
Butz et al. "Detection of allelic variations of human gene expression by polymerase colonies". 2004. *GMC Genetics.* 5. (5 pages).
Butz et al. "Detecting changes in the relative expression of KRAS2 splice variants using polymerase colonies". 2004. *Biotechnol. Prog.* 20:1836-1839.
Butz et al. Characterization of Mutations and loss of heterozygosity of p53 and K-ras2 in Pancreatic Cancer Cell Lines by Immobilized PCR. 2003. *BMC Biotechnol.* 3:11. (6 pages).
Cao et al. "Electronic sensitivity of carbon nanotubes to internal water wetting". 2011. *ACS Nano.* 5(4):3113-3119.
Carroll et al. "Droplet-based microfluidics for emulsion and solvent evaporation synthesis of monodisperse mesoporous silica microspheres". 2008. *Langmuir.* 24:658-661.
Carroll et al. In Structure and Functional Properties in Colloidal Systems (ed R. Hidalgo-Alvarez) (Taylor and Francis). 2009. Surfactant Science Series, vol. 146. Title Page, Copyright Page, Table of Contents. (4 pages).
Chaisson et al. "De novo fragment assembly with short mate-paired reads: Does the read length matter?" 2009. *Genome Research.* 19:336-346.
Chaisson et al. "Short read fragment assembly of bacterial genomes". 2008. *Genome Research.* 18:324-330.
Clarke et al. "Continuous base identification for single-molecule nanopore DNA sequencing". 2009. *Nat Nanotechnol.* 4:265-270.
Consortium. "A map of human genome variation from population-scale sequencing". 2010. *Nature.* 467:1061-1073.
Cripe et al. "Transcriptional Activation of the Human Papillomavirus-16 P97 Promoter by an 88-Nucleotide Enhancer Containing Distinct Cell-Dependent and AP-1-Responsive Modules". 1990. *The New Biologist.* 2(5):450-461.
Crusius et al. "The Human Papillomavirus Type 16 E5-Protein Modulates Ligand-Dependent Activation of the EGF Receptor Family in the Human Epithelial Cell Line HaCaT". 1998. *Experimental Cell Research.* 241:76-83.
Dapprich et al. "SNP-specific extraction of haplotype-resolved targeted genomic regions". 2008. *Nucleic Acids Research.* 36(15):e94. (9 pages).
Das et al. "Single molecule linear analysis of DNA in nano-channel labeled with sequence specific fluorescent probes". 2010. *Nucleic Acids Research.* 38(18):e177. (8 pages).
Dean et al. "Rapid amplification of plasmid and phage DNA using Phi29 DNA polymerase and multiply-primed rolling circle amplification". 2001. *Genome Res.* 11:1095-1099.
Denisov et al. "Consensus generation and variant detection by Celera Assembler". 2008. *Bioinformatics.* 24:1035-1040.
Diehl et al. "BEAMing: single-molecule PCR on microparticles in water-in-oil emulsions". 2006. *Nat Methods.* 3(7):551-559.
Doi et al. "STABLE: protein-DNA fusion system for screening of combinatorial protein libraries in vitro". 1999. *FEBS Lett* 457:227-230.
Doorbar et al. "The Biology and Life-Cycle of Human Papillomaviruses" 2012. Vaccine 305:F55-F70.

(56) References Cited

OTHER PUBLICATIONS

Drummond et al. "Electrochemical DNA sensors". 2003. *Nature Biotechnology*. 21(10):1192-1199.
Eichler et al. "A haplotype map of the human genome". 2005. *Nature*. 437:1299-1320.
Eid et al. "Real-time DNA sequencing from single polymerase molecules". 2009. *Science*. 323:133-138.
Ellis et al. "Localization of breast cancer susceptibility loci by genome-wide SNP linkage disequilibrium mapping". 2006. *Genet. Epidemiol*. 30:48-61.
Fernandez-Ortuno et al. "Multiple displacement amplification, a powerful tool for molecular genetic analysis of powdery mildew fungi". 2007. *Current Genetics*. 51:209-219.
Flusberg et al. "Direct detection of DNA methylation during single-molecule, real-time sequencing". 2010. *Nature Methods*. 7(6):461-465.
Foster et al. "Whole genome amplification from filamentous fungi using Phi29-mediated multiple displacement amplification". 2005. *Fungal Genet Biol*. 42:367-375.
Fritz et al. "Electronic detection of DNA by its intrinsic molecular charge". 2002. *Proc Natl Acad Sci USA*. 99(22):14142-14146.
Gabriel et al. "The structure of haplotype blocks in the human genome". 2002. *Science*. 296:2225-2229.
Garaj et al. "Graphene as a subnanometre trans-electrode membrane". 2010. *Nature*. 467:190-193.
Genther et al. "Quantitative Role of the Human Papillomavirus Type 16 E5 Gene during the Productive Stage of the Viral Life Cycle". 2003. Journ. Of Virology. 77(5):2832-2842.
Gonzalez et al. "Multiple displacement amplification as a pre-polymerase chain reaction (pre-PCR) to process difficult to amplify samples and low copy number sequences from natural environments". 2005. *Environ Microbiol*. 7(7):1024-1028.
Guo et al. "An integrated system for DNA sequencing by synthesis using novel nucleotide analogues". 2010. *Acc Chem Res* 43(4):551-563.
Guo et al. "Four-color DNA sequencing with 3'-O-modified nucleotide reversible terminators and chemically cleavable fluorescent dideoxynucleotides". 2008. *Proc Natl Aca Sci USA* 105(27):9145-9150.
Ju et al. "Four-color DNA sequencing by synthesis using cleavable fluorescent nucleotide reversible terminators". 2006. *Proceed of Natl Acad of Sciences of USA*. 103(52):19635-19640.
Healey. "Nanopore-based single-molecule DNA analysis". 2007. *Nanomedicine (Lond)*. 2:459-481.
Hildesheim et al. "Effect of Human Papillomavirus 16/18 L1 Virus like Particle Vaccine Among Young Women with Preexisting Infection". 2007. *JAMA*. 208(7):743-753.
Hinds et al. "Whole-genome patterns of common DNA variation in three human populations". 2005. *Science*. 307:1072-1079.
Hussain et al. "TP53 mutations and hepatocellular carcinoma: insights into the etiology and pathogeneiss of liver cancer". 2007. *Oncogene*. 26:2166-2176.
Hutchison et al. "Cell-free cloning using phi29 DNA polymerase". 2005. *Proceed of the Nat Acad of Sciences of USA*. 102(48):17332-17336.
Hynes et al. "ErbB receptors and signatling pathways in cancer". 2009. *Current Opinion in Cell Biology*. 21:177-184.
Imelfort et al. "De novo sequencing of plant genomes using second-generation technologies". 2009. *Briefings in Bioinformatics*. 10(6):609-618.
Jiang et al. "Genome amplification of single sperm using multiple displacement amplification". 2005. *Nucleic Acids Res*. 33(10):e91. (9 pages).
Kapranov. "Studying chromosome-wide transcriptional networks: new insights into disease?" 2009. *Genome Med*. 1:50. (4 pages).
Kapranov. "From transcription start site to cell biology". 2009. *Genome Biology*. 10:217. (4 pages).
Kelly et al. "Miniaturizing chemistry and biology in microdroplets". 2007. *Chemical Communications (Cambridge, England)*. 1773-1788.
Kim et al. "Amplification Methods Bias Metagenomic Libraries of Uncultured Single-Stranded and Double-Stranded DNA Viruses". 2011. *Applied and Environ. Microbiology*.77(21):7663-7668.
Kitzman et al. "Haplotype-resolved genome sequencing of a Gujarati Indian individual". 2011. *Nature Biotechnology*. 29(1):59-63.
Korlach et al. "Real-time DNA sequencing from single polymerase molecules". 2010. *Methods in Enzymology*. 472:431-455.
Kyo et al. "Expression of AP1 during cellular differentiation determines human papillomavirus E6/E7 expression in stratified epithelial cells". 1997. *Journ. Of General Virology*. 78:401-411.
Lage et al. "Whole genome analysis of genetic alterations in small DNA samples using hyperbranched strand displacement amplification and array-CGH". 2003. *Genome Research*. 13:294-307.
Lander et al. "Initial sequencing and analysis of the human genome". 2001. *Nature*. 409:860-921.
Langmead. "Aligning short sequencing reads with Bowtie". 2010. *Curr. Protoc Bioinformatics*. Chapter 11, Unit 11 17. (24 pages).
Langmead et al. "Ultrafast and memory-efficient alignment of short DNA sequences to the human genome". 2009. *Genome Biology*. 10:R25. (10 pages).
Levy et al. "The diploid genome sequence of an individual human". 2007. *PLoS Biology*. 5(10):e254:2113-2144.
Lewis. "Signal transduction through MAP kinase cascades". 1998. 74:49-139.
Li et al. "BEAMing up for detection and quantification of rare sequence variants". 2006. *Nat Methods*. 3(2):95-97.
Li et al. "Fast and accurate long-read alignment with Burrows-Wheeler transform". 2010. *Bioinformatics*. 26(5):589-595.
Li et al. "Fast and accurate short read alignment with Burrows-Wheeler transform". 2009. *Bioinformatics*. 25(14):1754-1760.
Lin et al. "Comparative studies of de novo assembly tools for next-generation sequencing technologies". 2011. *Bioinformatics*. 27(15):2031-2037.
Link et al. "Electric control of droplets in microfluidic devices". 2006. *Chem. Int. Ed*. 45:2556-2560.
Lipson et al. "Quantification of the yeast transcriptome by single-molecule sequencing". 2009. *Nature Biotechnology*. 27(7):652-658.
Liu et al. "Translocation of single-stranded DNA through single-walled carbon nanotubes". 2010. *Science*. 327:64-67.
Luan et al. "Control and reversal of the electrophoretic force on DNA in a charged nanopore". 2010. *J Phys. Condens Matter*. 22:454123. (6 pages).
MacDonald et al. "The Huntington's disease candidate region exhibits many different haplotypes". 1992. *Nature Genetics*. 1:99-103.
Marcy et al. "Nanoliter reactors improve multiple displacement amplification of genomes from single cells". 2007. *PLoS Genet* 3(9):1702-1708.
Mazutis et al. "Multi-step microfluidic droplet processing: kinetic analysis of an in vitro translated enzyme". 2009. *Lab Chip*. 9:2902-2908.
McKernan et al. "Sequence and structural variation in a human genome uncovered by short-read, massively parallel ligation sequencing using two-base encoding". 2009. *Genome res*. 19:1527-1541.
Margulies et al. "Genome sequencing in microfabricated high-density picolitre reactors". 2005. *Nature*. 437:376-380.
McNally et al. "Optical recognition of converted DNA nucleotides for single-molecule DNA sequencing using nanopore arrays". 2010. *Nano Lett*. 10:2237-2244.
Meira et al. "Different antiproliferative effects of matuzumab and cetuximab in A431 cells are associated with persistent activity of the MPAK pathway". 2009. *European Journ. Of Cancer*. 45:1265-1273.
Meira et al. "Combination of cetuximab with chemoradiation, trastuzumab or MAPK inhibitors: mechanisms of sensitisation of cervical cancer cells". 2009. *British Journ. Of Cancer*. 101:782-791.
Merchant et al. "DNA translocation through graphene nanopores". 2010. *Nano Lett*. 10:2915-2921.
Merritt et al. "Parallel competition analysis of *Saccharomyces cerevisiae* strains differing by a single base using polymerase colonies". 2003. *Nucleic Acids Res*. 31(15):e84. (8 pages).

(56) References Cited

OTHER PUBLICATIONS

Merritt et al. "Parallel analysis of tetramerization domain mutants of the human p53 protein using PCR colonies". 2007. *Genomic Medicine*. 1:113-124.
Merritt et al. "Parallel analysis mutant human glucose 6-phosphage dehydrogenase in yeast using PCR colonies" 2005. *Biotech Bioeng* 92(5):519-531.
Merritt et al. "Assaying gene function by growth competition experiment". 2004. *Metab Eng* 6:212-219.
Merritt et al. "Loss of Antibody Productivity is Highly Reproducible in Multiple Hybridoma Subclones". 1993. *Biotech and Bioeng*. 42:247-250.
Mikkilineni et al. "Digital Quantitative Measurements of Gene Expression". 2004. *Biotech Bioeng*. 86(2):117-124.
Mikolajick et al. "The pH-sensing properties of tantalum pentoxide films fabricated by metal organic low pressure chemical vapor deposition". 1997. *Sens Actuators B Chem*. 44:262-267.
Milla et al. "Use of the restriction enzyme AvaI and Exo-Bst polymerase in strand displacement amplification". 1998. *BioTechniques*. 24(3):392-396.
Milos. Helicos BioSciences. *Pharmacogenomics*. 2008. 9(4)477-480.
Mitra et al. "Digital genotyping and haplotyping with polymerase colonies". 2003. *Proc. Natl. Acad. Sci. USA*. 100(10):5926-5931.
Monstein et al. "Multiple displacement amplification of DNA from human colon and rectum biopsies: bacterial profiling and identification of *Helicobacter pylori*-DNA by means of 16S rDNA-based TTGE and pyrosequencing analysis". 2005. *J. Microbiol. Methods*. 63:239-247.
Morozova et al. "Applications of next-generation sequencing technologies in functional genomics". 2008. *Genomics*. 92:255-264.
Nilsson et al. "Multiple displacement amplification of isolated DNA from human gallstones: molecular identification of Helicobacter DNA by means of 16S rDNA-based pyrosequencing analysis". 2005. *Helicobacter*. 10(6):592-600.
Orlando et al. "True single-molecule DNA sequencing of a Pleistocene horse bone". 2011. *Genome Research*. 21:1705-1719.
Ozsolak et al. "Comprehensive polyadenylation site maps inyeast and human reveal pervasive alternative polyadenylation". 2010. *Cell*. 143:1018-1029.
Ozsolak et al. "Amplification-free digital gene expression profiling from minute cell quantities". 2010. *Nature Methods*. 7(8):619-621.
Pan et al. "A procedure for highly specific, sensitive, and unbiased whole-genome amplification". 2008. *Proc Natl. Aca Sci USA*. 105(40):15499-15504.
Paez et al. "EGFR Mutations in Lung Cancer: Correlation with Clinical Response to Gefitinib Therapy". 2004. *Science*. 304:1497-1500.
Pang et al. "Towards a comprehensive structural variation map of an individual human genome". 2010. *Genome Biol*. 11:R52. (14 pages).
Peto et al. "Epidermal growth factor induction of human papillomavirus type 16 E6/E7 mRNA in tumour cells involves two AP-1 binding sites in the viral enhancer". 1995. *Journ. Of General Virology*. 76:1945-1958.
Pim et al. "Human papillomavirus type 16 E5 gene stimulates the transforming activity of the epidermal growth factor receptor". 1991. *Oncogene*. 7:15-23.
Porreca et al. "Polony DNA sequencing". 2006. Current protocols in molecular biology / edited by Frederick M. Ausubel. 7.8.1-7.8.22 (22 pages).
Pourmand et al. "Direct electrical detection of DNA synthesis". 2006. *Proc Natl Acad Sci USA*. 103(17):6466-6480.
Purushothaman et al. "Protons and single nucleotide polymorphism detection; A simple use for the ion sensitive field effect transistor". 2006. *Sens Actuators B Chem*. 114:964-968.
Raymond et al. "Epidermal Growth Factor Receptor Tyrosine Kinase as a Target for Anticancer Therapy". 2000. *Drugs. 60 Suppl.* 1:15-23.
Rhode et al. "Open-source genomic analysis of Shiga-toxin-producing *E.coli*". 2011. *New England Journ. Of Medicine*. 365:718-724.
Robinson. "Semiconductors charge into sequencing". 2011. *Nat. Biotechnol*. 29(9):805-807.
Rodrigue et al. "Whole genome amplification and de novo assembly of single bacterial cells". 2009. *PLoS ONE*. 4(9):e6864. (10 pages).
Rodriguez et al. "A specific subdomain in phi29 DNA polymerase confers both processivity and strand-displacement capacity". 2005. *Proc Natl. Acad Sci USA*. 102(18):6407-6412.
Rosenberger et al. "Alternative splicing of human papillomavirus type-16 E6/E6 early mRNA is coupled to EGF signaling via Erk 1/2 activation". 2010. *PNAS*. 107(15):7006-7011.
Rothberg et al. "An integrated semiconductor device enabling non-optical genome sequencing". 2011. *Nature*. 475:348-352.
Ruffalo et al. "Comparative analysis of algorithms for next-generation sequencing read alignment". 2011. *Bioinformatics*. 27(20):2790-2796.
Ruparel et al. "Design and synthesis of a 3'-O-allylphotocleavable fluorescent nucleotide as a reversible terminator for DNA sequencing by synthesis". 2005. *Proceed of Natl Acad of Sciences of USA*. 102(17):5932-5937.
Sakata et al. "DNA sequencing based on intricate molecular charges". 2006. *Angew. Chem. Int. Ed*. 45:2225-2228.
Sakurai et al. "Real-time monitoring of DNA polymerase reactions by a micro ISFET pH sensor". 1992. *Anal Chem*. 64:1996-1997.
Schadt et al. "A window into third-generation sequencing". 2010. *Human molecular genetics*. 19(2):R227-240.
Schadt et al. "Computational solutions to large-scale data management and analysis". 2010. *Nature Reviews. Genetics*. 11:647-657.
Seo et al. "Four-color DNA sequencing by synthesis on a chip using photocleavable fluorescent nucleotides". 2005. *Proceed of Natl Acad of Sciences of USA*. 102(17):5926-5931.
Shearer et al. "Comprehensive genetic testing for hereditary hearing loss using massively parallel sequencing". 2010. *Proc. Natl. Acad. Sci. USA*. 107:21104-21109.
Shendure et al. "Overview of DNA sequencing strategies". 2008. Current protocols in molecular biology / edited by Frederick M. Ausubel. Chapter 7. Unit 7 1. (23 pages).
Shendure et al. "Accurate multiplex polony sequencing of an evolved bacterial genome". 2005. *Science*. 309:1728-1732.
Skantar et al. "Multiple displacement amplification (MDA) of total genomic DNA from *Meloidogyne* spp. And comparison to crude DNA extracts in PCR of ITS1, 28SD2-D3 rDNA and Hsp90". 2005. *Namatology*. 7(2):285-293.
Spits et al. "Optimization and evaluation of single-cell whole-genome multiple displacement amplification". 2006. *Human Mutation*. 27(5):496-503.
Steinmann et al. "Helicos single-molecule sequencing of bacterial genomes". 2011. *Methods in molecular biology*. 733:3-24.
Straight et al. "The E5 oncoprotein of human papillomavirus type 16 transforms fibroblasts and effects the downregulation of the epidermal growth factor receptor in keratinocytes". 1993. *J. Virol*. 67(8):4521-4532.
Stram et al. "Choosing haplotype-tagging SNPS based on unphased genotype data using a preliminary sample of unrelated subjects with an example from the Multiethnic Cohort Study". 2003. *Hum Hered*. 55:27-36.
Suk et al. "A comprehensively molecular haplotype-resolved genome of a European individual". 2011. *Genome Research*. 21:1672-1685.
Tawfik et al. "Man-made cell-like compartments for molecular evolution". 1998. *Nat Biotechnol*. 16:652-656.
Tewhey et al. "The importance of phase information for human genomics". 2011. *Nat Rev Genet* 12:215-223.
Thiam et al. "Breaking of an emulsion under an ac electric field". 2009. *Phys Rev Lett*. 102:188304-1 to 188304-4.
Thierry et al. "Two AP1 sites binding JunB are essential for human papillomavirus type 18 transcription in keratinocytes". 1992. *J. Virol*. 66(6):3740-3748.
Thompson et al. "The properties and applications of single-molecule DNA sequencing". 2011. *Genome Biology*. 12:217. (10 pages).

(56) References Cited

OTHER PUBLICATIONS

Thompson et al. "Single-step capture and sequencing of natural DNA for detection of BRCA1 mutations". 2011. *Genome Research*. 22:340-345.

Thomsen et al. "A floating gate MOSFET with tunneling injector fabricated using a standard double-polysilicon CMOS process". 1991. *IEEE Electron Device Letters*. 12(3):111-113.

Turner et al. "Assaying chromosomal inversions by single-molecule haplotyping". 2006. *Nature Methods*. 3(6):439-445.

Venter et al. "The sequence of the human genome". 2001. Science. 291:1304-1351.

Vicenzi et al. "The biological properties of cetuximab". 2008. *Critical Reviews in Oncology/Hematology*. 68:93-106.

Wang et al. "Efficient on-demand compound droplet formation: from microfluidics to microdroplets as miniaturized laboratories". 2009. *Small*. 5(10):1149-1152.

Waterston et al. "Initial sequencing and comparative analysis of the mouse genome". 2002. *Nature*. 420:520-562.

Xu et al. "Dual primer emulsion PCR for next-generation DNA sequencing". 2010. *Biotechniques*. 48(5):409-412.

Xu et al. "A Readout Integrated Circuit (ROIC) with Hybrid Source/Sensor Array". 2011. Annual Meeting of the IEEE Photonic Society. (2 pages).

Yu et al. "Positional cloning of the Werner's syndrome gene". 1996. *Science*. 272:258-262.

Zagnoni et al. "On-chip electrocoalescence of microdroplets as a function of voltage, frequency and droplet size". 2009. *Lab Chip*. 9:2652-2658.

Zarkesh-Ha et al. "A Reconfigurable ROIC for Integrated Infrared Spectral Sensing". 2010. $23^{rd}$ Annual Meeting of the IEEE Photonic Society. 714-715.

Zur Hausen. "Papillomaviruses as Carcinomaviruses". 1989. Advances in Viral Oncology. 15 pages.

Zhang et al. "Long-range polony haplotyping of individual human chromosome molecules". 2006. *Nat. Genet*. 38(3):382-387.

Zhang et al. "A practical comparison of de novo genome assembly software tools for next-generation sequencing technologies". 2011. *PLoS ONE*. 6(3):e17915. (12 pages).

Zhang et al. "Sequencing genomes from single cells by polymerase cloning". 2006. *Nat Biotechnol*. 24(6):680-686.

Xie et al., "InGaAs/InAl As Avalanche Photodiode With Low Dark Current for High-Speed Operation", *IEEE Photonics Technology Letters*, Aug. 15, 2015; 27(6):1745-1748.

\* cited by examiner

DOUBLE GATE ION SENSITIVE FIELD EFFECT TRANSISTOR

This application is the § 371 U.S. National Stage of International Application No. PCT/US2012/057758, filed 28 Sep. 2012, which claims the benefit of U.S. Provisional Application No. 61/542,013, filed 30 Sep. 2011, and 61/550,166, filed 21 Oct. 2011, each of which are incorporated by reference herein in their entireties.

BACKGROUND

Ion sensitive field effect transistors (ISFETs) provide a non-optical based sequencing technique which has good run times and high per-base accuracy. Currently, ISFETs are commercially available in sequencing chips that have 1.3 million and 6.3 million ISFET sensors. In order to render DNA sequencing even more cost-effective, sequencing chips with even more ISFETS per chip are desirable.

SUMMARY

Disclosed herein are devices that include a substrate; a source region and a drain region formed within the substrate and having a channel region provided therebetween; a first insulating layer formed over the channel region; a first floating gate formed over the first insulating layer, the first floating gate configured to respond to an analyte in a target material; and a second gate formed over the first floating gate, the second gate capacitively coupled but not electrically connected to the first floating gate.

Also disclosed is a method of determining the concentration of an analyte in a target material, the method including the steps of providing a disclosed device; applying a potential of about 0 V to the second gate; monitoring the current flowing through the channel region between the source and the drain; and determining the concentration of the analyte in the target material based on the monitored current.

Also disclosed are arrays that can include a plurality of disclosed devices; and at least one readout circuit, the readout circuit configured to monitor current flowing through the channel region between the source and the drain in at least one of the plurality of devices.

The above summary is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

"Include," "including," or like terms means encompassing but not limited to, that is, including and not exclusive.

Disclosed herein are ion sensitive field effect transistors (ISFETs) that include a double gate. The second gate, with the floating gate being the first gate, can function as an access transistor for the ISFET device, thereby decreasing the size of an individual device footprint. Such a reduced footprint size can allow arrays with more ISFETS per area. Also disclosed here are methods of monitoring analytes in a target material that can offer lower detection limits thereby allowing for detection in smaller sample sizes.

ISFET devices are impedance transformation devices that operate in a manner similar to that of a metal oxide semiconductor field effect transistor (MOSFET), and are particularly configured to selectively measure ion activity in a solution (for example, hydrogen ions in a solution).

Figure 1:
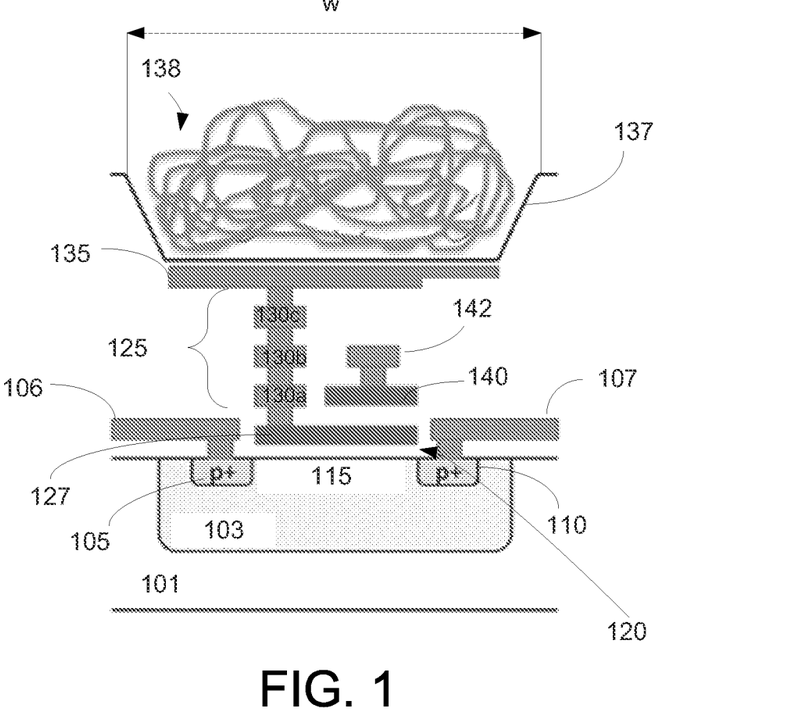
FIG. 1 depicts a cross sectional view of an exemplary ion-sensitive field effect transistor (ISFET) device disclosed herein.

FIG. 1 depicts a cross sectional view of an exemplary ion-sensitive field effect transistor (ISFET) device 100. Devices such as that depicted in FIG. 1 can be fabricated using conventional CMOS (complementary metal oxide semiconductor) processes, for example. Assuming a CMOS fabrication, the device can include a substrate 101, for example a p-type silicon substrate. An n-type well 103 is formed into the substrate to form the body of the device. Highly doped p-type regions form a source 105 and a drain 110. Metal contacts 106 and 107 are formed to provide electrical connection to the source and the drain. A channel region 115 is located between the source and the drain within the body of the substrate. A first insulating layer 120 is formed over the channel region. The first insulating layer can be formed of an oxide for example. The first insulating layer can also be referred to as the gate oxide, because as indicated below it is between the first floating gate and the body (i.e., substrate) of the device. The first insulating layer 120 can, but need not be, part of a larger structure. For example, in the device depicted in FIG. 1, the "white" space between the metal contacts and the ion sensitive membrane can generally be made of an insulating material. The first insulating layer 120 can, but need not be, a portion of that larger area of that insulating material.

A first floating gate 127 is formed over the first insulating layer. The first floating gate includes a polysilicon gate formed directly over the first insulating layer. The first floating gate can be coupled to multiple metal layers 130$a$, 130$b$, and 130$c$ disposed within an oxide layer, which can collectively be referred to as the first floating gate structure 125. The first floating gate, and the first floating gate structure are configured to create or initiate or utilize the ion sensitive field effect. The first floating gate structure, and the first floating gate are referred to as "floating" because they are electrically isolated from other conductors associated with the ISFET. The first floating gate structure is disposed between the first insulating layer and the ion sensitive membrane 135. Analytes in a target material 138 in contact with the ion-sensitive membrane, particularly right above the floating gate structure, alters the electrical characteristics of the device, causing a current to flow through the channel region between the source and the drain.

Disclosed devices can also include a second gate 140. The second gate 140 is formed over the first floating gate 127, but not in electrical connection with the first floating gate 127. The second gate can be capacitively coupled to the first gate. The second gate 140 can be connected, via an access contact 142 to a control voltage, $V_{CTRL}$. The voltage of $V_{CTRL}$ affects the functioning of the first floating gate 127. For example, if $V_{CTRL}$ is set to an "on" voltage, current is able to flow in the channel region between the source and the drain. If $V_{CTRL}$ is set to an "off" voltage, current is not able to flow in the channel region between the source and the drain. In this way, the second gate 140 can act as an access transistor for the ISFET. By controlling the voltage on the second gate, the ISFET can either be read from, or not. In some embodiments, an on voltage can be about 0 V. In some embodiments, when $V_{CTRL}$ is greater than about 0 V, less current flows through the channel region between the source and the drain than when $V_{CTRL}$ is about 0 V. In some embodiments, when $V_{CTRL}$ is about 5 V or greater, current cannot flow through the channel region between the source and the drain.

Figure 2:
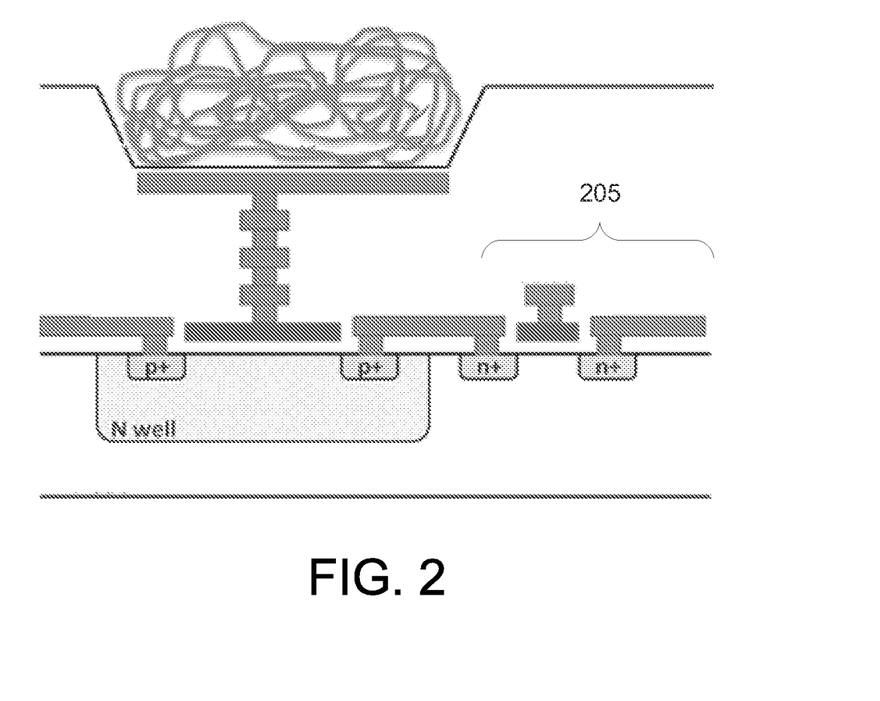
FIG. 2 depicts a cross sectional view of an ISFET device of the prior art.

FIG. 2 depicts a prior art ISFET device. Components similar to those discussed above are not specifically enumerated or labeled herein. ISFET devices of the prior art, such as that depicted in FIG. 2 would generally be fabricated in electrical connection with a separate access transistor 205. The access transistor in this prior art device functions to allow the ISFET device to be read, i.e., it allows it to carry a current and therefore detect the presence of the analyte in the target material. As seen in the device depicted in FIG. 2, the prior art device, because of the necessity of being configured with the separate access transistor, has a larger sensor area than that of devices disclosed herein. In contrast to the depicted prior art device, disclosed devices do not need a separate access transistor.

Disclosed devices can be configured with a well. The device depicted in FIG. 1 includes a well 137. A well can generally be positioned over the first floating gate structure 125 and over the ion sensitive membrane 135. Such a configuration allows ions in the well to pass through the ion sensitive membrane and act on the first floating gate structure and ultimately the first floating gate, thereby allowing (assuming that $V_{CTRL}$ is set to an on value) current to flow between the source and the drain. The amount of current flowing between the source and the drain is indicative of the amount of ions (for example hydrogen ions) in the target material in the well. The well can generally have any configuration that can house or contain at least some volume of target material.

Devices disclosed herein can be fabricated or utilized in an array format. Disclosed devices, because they do not necessarily have to include a separate access transistor, may have advantages over previously utilized devices because a single device can have a smaller area. This can be advantageous when the devices are being formed in an array of devices, because smaller devices can allow more devices to be packed into the same overall space. A disclosed array can include a plurality of devices. Any convenient number of devices can be included in an array. In some embodiments, an array can include $10^3$ (thousands) of devices, $10^6$ (millions "M" of devices), or $10^9$ (billions "B" of devices). In some embodiments, an array can include $10^6$ or even $10^9$ devices in an area that is on the order of a square inch. Disclosed arrays can be two dimensional or three dimensional arrays.

In some embodiments, a well and the associated device can be scalable, meaning the size can be decreased as afforded by processing techniques. The size of a device can be characterized by the size of the well. In some embodiments, the well can be characterized by the width of the well. The width of the well 137 in FIG. 1 is given by the dimension w. In some embodiments, the width of a well can be less than 5 micrometers (μm). In some embodiments, the width of a well can be less than 4 μm. In some embodiments, the width of a well can be less than 3 μm. In some embodiments, the width of a well can be a few μm or less. In some embodiments, the width of a well can be about 1 μm or even less than 1 μm.

Disclosed devices can also include other additional components not discussed herein. Examples of such other components can include, for example a reference electrode, and various other electronic components. Alternatively or additionally, disclosed devices can include readout circuits (other than or in addition to those discussed herein), and power management components for example.

The above discussed components of disclosed devices can be fabricated using techniques and materials known to those of skill in the art. In some embodiments, silicon-on-insulator (SOI), or silicon-on-sapphire (SOS) technology can be utilized. As examples of fabrication methods and steps that can be utilized herein, in some embodiments, a standard 90 nm CMOS process by Taiwan Semiconductor Manufacturing Corporation (TSMC) through MOSIS can be utilized. The second gate can be constructed by the second poly step offered in double poly CMOS processes. Similarly, in some embodiments, the second gate can be constructed by the first metal (M1) layer in standard CMOS processes. Generally, components of the device can be fabricated from materials commonly utilized for such components. In some embodiments, the second gate can be made of the same materials that the first floating gate is made of, for example, polysilicon. In some embodiments, ion sensitive membranes can be fabricated from a metal oxide, or nitride. In some embodiments, the ion sensitive membrane can be fabricated from $Ta_2O_5$, $SiO_2$, $Al_2O_3$, $HfO_2$, $TiO_2$, or $Si_3N_4$. In some embodiments, the ion sensitive membrane can be fabricated from $Ta_2O_5$.

Disclosed arrays can also be configured along with various methods and/or electronics for monitoring the current flowing through the channel region of each device, or more specifically, for example for reading the pH values of each well. Readout speed can be problematic in such arrays. The nucleotide incorporation transient normally takes place within about 5 seconds. It can therefore be important to capture enough data form all sensors (in the case of a $10^9$ array, all $10^9$ sensors) in about 5 seconds. In a $10^9$ array, that implies that the unit cell readout time is only 50 picoseconds (ps). In some embodiments, disclosed arrays can therefore be implemented with multiple or a plurality of parallel readout circuits. In some embodiments, a $10^9$ array can be implemented with at least 20 parallel readout circuits. In some embodiments, a $10^9$ array can be implemented with at least 40 parallel readout circuits. In some embodiments, a $10^9$ array can be implemented with 50 parallel readout circuits. In an exemplary $10^9$ array including 50 parallel readout circuits, the unit cell readout time would be about 2.5 nanoseconds (ns).

Disclosed devices can measure various analytes in a target material. Various analytes other than, or in addition to those discussed herein, can be sensed by selecting appropriate materials for the ion sensitive material. For example, ammonium can be detected, using for example aniline trimmers. In some embodiments, ionic analytes can be measured. In some embodiments, ionic analytes of interest can include, for example hydrogen ions or protons ($H^+$). Concentration of protons in a solution is often referred to by the pH, which is the −log of the hydrogen ion concentration. In embodiments where the analyte of interest is hydrogen ions, exemplary devices can function to detect relatively small amounts of hydrogen ions, for example on the order of $10^4$ hydrogen ions.

Also disclosed herein are methods of determining the concentration of an analyte in a target material. Disclosed methods can include use of or providing a disclosed device. A step of providing a device can include fabricating a device, procuring a device (whether via sale or otherwise), obtaining a device, or configuring a device to use it in a disclosed method.

Disclosed methods can also include a step of applying an "on" potential, or $V_{CTRL}$ of "on" to the second gate. As discussed above, when $V_{CTRL}$ is on, current is allowed to flow, in response to hydrogen ions (in such an example) in the target material in the well, between the source and the drain. If $V_{CTRL}$ is set to "off", current is no longer allowed to flow between the source and the drain. Disclosed methods can include additional, optional steps of applying a potential of greater than 0 V, or a $V_{CTRL}$ off voltage at some time after the $V_{CTRL}$ on was applied. Application of a $V_{CTRL}$ off will stop the current flowing through the channel region between the source and the drain.

Disclosed methods can also include a step of monitoring the current flowing through the channel region between the source and the drain. The amount of current flowing through the channel region can vary depending on the amount of analyte (hydrogen ions in such an example) in the target material. The amount of current can be monitored using known electronic components and/or mathematical methods.

Disclosed methods can also include a step of determining the concentration of the analyte in the target material based on the monitored current. In some embodiments, the current can increase as the amount of the analyte increases. In some embodiments where the analyte of interest is hydrogen ions, an increase amount of hydrogen ions (which would be a lower pH) can cause more current to flow through the channel region between the source and the drain. The concentration of the analyte in the target material can be determined, based on the monitored current using known electronic components and/or mathematical methods. Disclosed methods can also optionally include the additional step of converting the concentration of the analyte in the target material into a pH measurement. The concentration of the analyte in the target material can be converted into a pH measurement using known electrical components and/or mathematical methods.

Generally, disclosed devices also have a potential applied to the source and/or drain. Such potential(s) can be referred to as $V_{DS}$. $V_{DS}$ can also function to control the amount of current flowing through the channel region between the source and the drain in response to the concentration of the analyte in the target material. As $V_{DS}$ is increased, the amount of current flowing through the channel region in response to a given concentration of analyte in a target material is increased. Stated another way, at a constant analyte concentration, increasing the $V_{DS}$ will increase the current flowing through the channel region between the source and the drain.

It is thought, but not relied upon that use of relatively high $V_{DS}$ may allow the device to function in "avalanche" mode. A device functioning in avalanche mode can allow the signal to be amplified. This could allow disclosed devices to detect smaller amounts of analytes in the target material. Avalanche mode allows a signal caused by a proton(s) interacting with the ion sensitive material to be amplified. More specifically, avalanche buildup and impact ionization phenomena can be used to amplify the detected signal inside the channel region of the device. When VDS is set to the point of avalanche breakdown, the large electric field in the channel region of the device can cause a single electron (or hole) to have enough energy to generate another electron-hole pair by impact ionization. These events can then continue until the current is amplified to an extent that it can be monitored, as discussed above. In some embodiments, $V_{DS}$ can be set to at least about 5 V in order to cause the device to operate in avalanche mode. In some embodiments, $V_{DS}$ can be set to at least about 6 V in order to cause the device to operate in avalanche mode.

In some embodiments, once the current through the channel region is detected, the potential applied to the source and the drain can be reduced. Reducing the potential on the source and the drain can serve to quench the avalanche mode. This can allow the device to be prepared for another cycle of monitoring the current.

Disclosed embodiments of the method that utilize the relatively high $V_{DS}$ in order to allow the device to function in avalanche mode can be advantageous because they should have a lower signal to noise ratio because the amplification takes place at the sensor itself. Furthermore, because no additional or modified structures are necessary in the device itself, the method can be utilized with any ion sensitive field effect transistor. In some embodiments, methods that utilize relatively high $V_{DS}$ in order to allow the device to function in avalanche mode can be utilized in combination with disclosed devices that include a second gate. Such a combination would afford an array that can include $10^9$ devices having very small dimensions but would still afford a method of detection for very limited sample sizes.

Disclosed ISFETs can be utilized for any applications in which a component of a sample is to be monitored. Such applications can include applications in chemistry or biology, or more specifically, in monitoring various chemical or biological reactions, or in identifying, detecting, or even measuring various compounds. ISFETs may be utilized, for example, for monitoring reactions, including nucleic acid (e.g., DNA) sequencing reactions by monitoring components present, generated or used during a reaction. Furthermore, other chemical or biological processes can be monitored, for example, biological or chemical reactions, cell or tissue culture monitoring, neural activity monitoring, etc. Disclosed ISFETs may also be utilized to monitor components of samples from various sources, including for example clinical samples such as blood, urine, etc.; environmental samples such as water, soil or plant digests; and food processing samples.

The present disclosure is illustrated by the following examples. It is to be understood that the particular examples, materials, amounts, and procedures are to be interpreted broadly in accordance with the scope and spirit of the invention as set forth herein.

EXAMPLES

Simulation

Figure 3A:
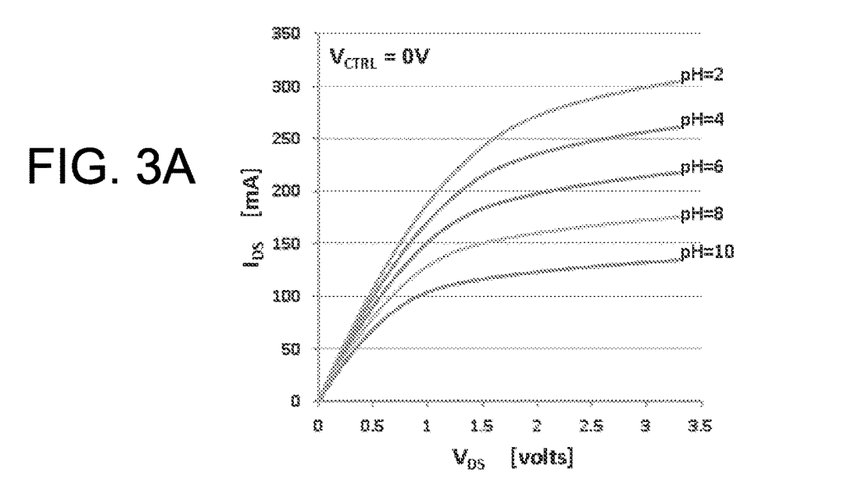
FIGS. 3A through 3C show simulation results of current ($I_{DS}$) versus potential on the source and/or drain ($V_{DS}$) for disclosed devices at different $V_{CTRL}$.
Figure 3B:
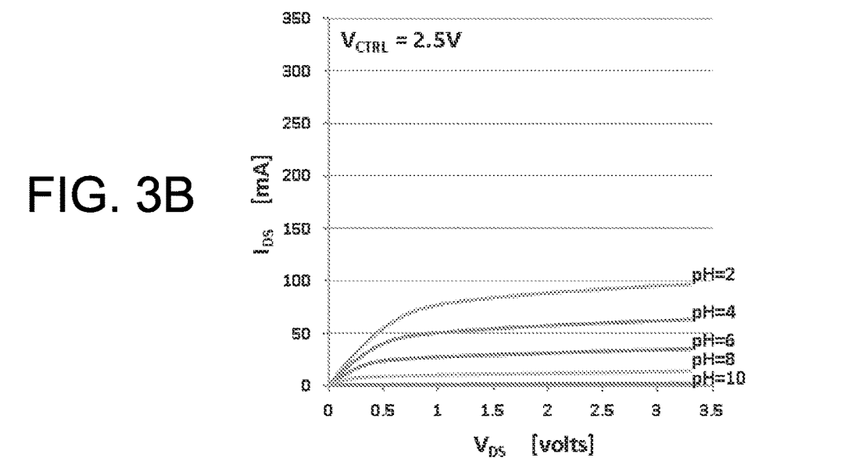
Figure 3C:
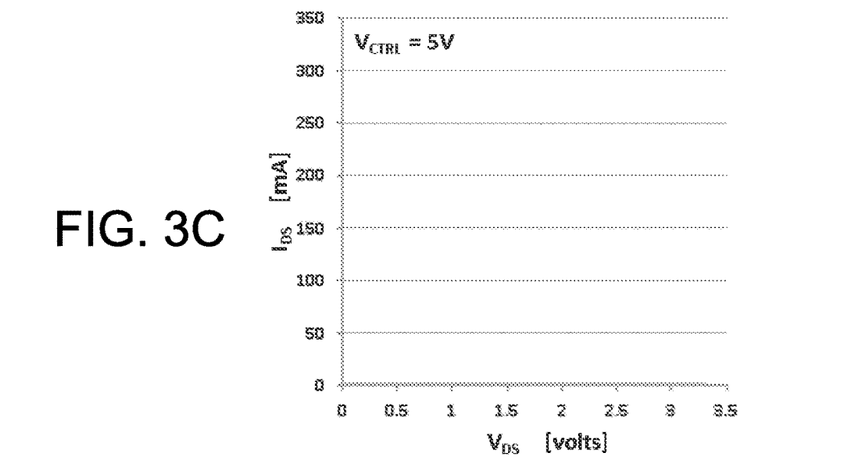

The functioning of a device, such as that disclosed in FIG. 1 was simulated using a SPICE (Simulation Program with Integrated Circuit Emphasis) simulation. The device was assumed to be as depicted in FIG. 1 made from a 0.35 μm CMOS process from Taiwan Semiconductor Manufacturing Corporation (TSMC). The results of the simulation are shown in FIGS. 3A through 3C. As seen there, the highest sensitivity to protons is achieved when $V_{CTRL}$ is grounded. The sensor becomes disabled ($V_{CTRL}$ is set to "off") when $V_{CTRL}$ is at 5 V.

Prototype

A prototype $10^6$ array containing (1000×1000) devices, such as that disclosed in FIG. 1 (scalable to $10^9$) will be fabricated using 0.35 TSMC double poly CMOS processing through MOSIS. It will include wells having a width of 0.5 μm and a 0.8 μm center to center pitch. The wells will be coated with a tantalum oxide ($Ta_2O_5$) layer for proton sensitivity. In order to perform the readout of the complete array in a desirable time, a multi-channel readout technique will be used, where each channel will be responsible for a certain portion of the sensor data. The readout process will be similar to image data readout in a regular digital camera.

Thus, embodiments of double gate ion sensitive field effect transistors are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

What is claimed is:

1. A method of determining the concentration of an analyte in a target material, the method comprising the steps of:
   providing an ion-sensitive field effect transistor (ISFET) device, the device comprising:
   a substrate;
   a source region and a drain region formed within the substrate and having a channel region provided therebetween;
   a first insulating layer formed over the channel region;
   a first floating gate formed over the first insulating layer, wherein an analyte acting on the floating gate structure alters the electrical properties of the device, the first floating gate being electrically isolated from any conductors within the device;
   a second gate formed over the first floating gate, the second gate capacitively coupled but not electrically connected to the first floating gate;
   applying a potential of about 0 V to the second gate;
   applying a potential to the source and drain to cause the ISFET device to function in avalanche mode;
   monitoring the current flowing through the channel region between the source and the drain; and
   determining the concentration of the analyte in the target material based on the monitored current.

2. The method according to claim 1 further comprising applying a potential of greater than about 0 V to the second gate in order to stop current flowing through the channel region between the source and the drain.

3. The method according to claim 1 further comprising converting the concentration of the analyte in the target material into a pH measurement.

4. The method according to claim 1, wherein the potential applied to the source and drain is at least about 5 V to initiate avalanche in the device.

5. The method according to claim 4, wherein the potential applied to the source and drain is at least about 6 V.

6. The method according to claim 4, wherein the current through the channel region is monitored until it can be detected.

7. The method according to claim 6, wherein once the current is detected, the potential applied to the source and the drain is reduced.

* * * * *